US00PP19714P2

(12) United States Plant Patent
Henny et al.

(10) Patent No.: US PP19,714 P2
(45) Date of Patent: Feb. 17, 2009

(54) ***AGLAONEMA* PLANT NAMED 'UFSB2'**

(50) Latin Name: *Aglaonema hybrida*
Varietal Denomination: UFSB2

(75) Inventors: Richard J. Henny, Tavares, FL (US); Jianjun J. Chen, Apopka, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 12/074,407

(22) Filed: Mar. 3, 2008

(51) Int. Cl.
*A01H 5/00* (2006.01)

(52) U.S. Cl. ..... Plt./376
(58) Field of Classification Search ..... Plt./376
See application file for complete search history.

*Primary Examiner*—Kent L Bell
(74) *Attorney, Agent, or Firm*—C. A. Whealy

(57) ABSTRACT

A new and distinct cultivar of *Aglaonema* plant named 'UFSB2', characterized by its compact and symmetrically rounded plant habit; freely branching growth habit; relatively short internodes and petioles; leaves with silvery grey-colored centers and venal areas and green-colored margins; and petioles with green-colored edges and cream-colored centers.

2 Drawing Sheets

Botanical designation: *Aglaonema hybrida.*
Cultivar denomination: 'UFSB2'.

BACKGROUND OF THE INVENTION

The present invention relates to a new and distinct cultivar of *Aglaonema* plant, botanically known as *Aglaonema hybrida,* and hereinafter referred to by the name 'UFSB2'.

The new *Aglaonema* is a naturally-occurring branch mutation of the *Aglaonema hybrida* cultivar Silver Bay, not patented. The new *Aglaonema* was discovered and selected by the Inventors from within a population of plants of the cultivar Silver Bay in a controlled environment in Apopka, Fla.

Asexual reproduction of the new cultivar by tip cuttings in a controlled environment in Apopka, Fla. has shown that the unique features of this new *Aglaonema* are stable and reproduced true to type in successive generations of asexual reproduction.

SUMMARY OF THE INVENTION

The cultivar UFSB2 has not been observed under all possible environmental conditions. The phenotype may vary somewhat with variations in environment such as temperature and light intensity, without, however, any variance in genotype.

The following traits have been repeatedly observed and are determined to be the unique characteristics of 'UFSB2'. These characteristics in combination distinguish 'UFSB2' as a new and distinct cultivar of *Aglaonema:*

1. Compact and symmetrically rounded plant habit.
2. Freely branching growth habit.
3. Relatively short internodes and petioles.
4. Leaves with silvery grey-colored centers and venal areas and green-colored margins.
5. Petioles with green-colored edges and cream-colored centers.

Plants of the new *Aglaonema* differ from plants of the parent, the cultivar Silver Bay, in the following characteristics:

1. Plants of the new *Aglaonema* are smaller and more compact than plants of the cultivar Silver Bay.
2. Plants of the new *Aglaonema* are more freely branching than plants of the cultivar Silver Bay.
3. Plants of the new *Aglaonema* have shorter petioles than plants of the cultivar Silver Bay.
4. Plants of the new *Aglaonema* had shorter and narrower leaves than plants of the cultivar Silver Bay.

Plants of the new *Aglaonema* can also be compared to plants of the cultivar Silver Moon, disclosed in U.S. Plant Pat. No. 12,973. In side-by-side comparisons conducted in Apopka, Fla., plants of the new *Aglaonema* differed from plants of the cultivar Silver Moon in the following characteristics:

1. Plants of the new *Aglaonema* were more compact and denser than plants of the cultivar Silver Moon.
2. Plants of the new *Aglaonema* were more freely branching than plants of the cultivar Silver Moon.
3. Plants of the new *Aglaonema* had shorter internodes than plants of the cultivar Silver Moon.
4. Leaves of plants of the new *Aglaonema* were shorter and narrower than leaves of plants of the cultivar Silver Moon.

BRIEF DESCRIPTION OF THE PHOTOGRAPHS

The accompanying photographs illustrate the overall appearance of the new *Aglaonema*. These photographs show the colors as true as it is reasonably possible to obtain in colored reproductions of this type. Colors in the photographs may differ slightly from the color values cited in the detailed botanical description which accurately describe the colors of the new *Aglaonema.*

The photograph on the first sheet is a side perspective view of a typical plant of 'UFSB2' grown in a container.

The photograph on the second sheet is a close-up view of the base of a typical plant of 'UFSB2'.

DETAILED BOTANICAL DESCRIPTION

In the following description, color references are made to The Royal Horticultural Society Colour Chart, 2001 Edition, except where general terms of ordinary dictionary significance are used. The aforementioned photographs and following observations and measurements describe plants grown in containers in Apopka, Fla. during the summer and early autumn in a polyethylene-covered greenhouse. Plants were grown under conditions and practices which approximate those generally used in commercial *Aglaonema* production. During the production of the plants, day temperatures ranged from about 29° C. to 35° C., night temperatures ranged from about 18° C. to 26° C. and light levels were about 3,000 foot-candles. Plants were about 18 months old when the photographs and the detailed description were taken.

Botanical classification: *Aglaonema* hybrida cultivar UFSB2.

Parentage: Naturally-occurring branch mutation of the *Aglaonema hybrida* cultivar Silver Bay, not patented.

Propagation:

*Type.*—By tip cuttings.

*Time to initiate roots, summer.*—About 21 to 24 days at 25° C. to 35° C.

*Time to initiate roots, winter.*—About 35 to 40 days at 15° C. to 28° C.

*Time to produce a rooted young plant, summer.*—About 30 to 35 days at 25° C, to 35° C.

*Time to produce a rooted young plant roots, winter.*—About 40 to 45 days at 15° C. to 28° C.

*Root description.*—Abundant fleshy whitish-colored roots with finer lateral roots.

Plant description:

*Plant/growth habit.*—Compact and symmetrically rounded plant habit; broad inverted triangle. Vigorous, dense growth habit; suitable for 15-cm to 20-cm containers. New leaves initially upright, then arching outwardly to downwardly with development.

*Plant height, from soil level to top of leaf plane.*—About 30 cm to 37 cm.

*Plant diameter or spread.*—About 58 cm to 64 cm.

*Stem description.*—Branching habit: Plants of the new *Aglaonema* are freely basal branching with about 28 basal branches developing per plant. Aspect: Mostly upright. Strength: Strong; somewhat flexible. Length, soil level to junction to two youngest leaves: About 12 cm to 16 cm. Diameter: About 1.25 cm. Internode length: About 7 mm to 13 mm. Color, immature: Between 155C and 145B to 145C. Color, mature: Between 144C and 145C; with further development, 146B tinged with 163D.

*Cataphylls.*—Not observed.

Foliage description:

*Arrangement.*—Alternate/whorled; simple.

*Length.*—About 17 cm to 21 cm.

*Width (flattened).*—About 7 cm to 8.5 cm.

*Shape.*—Elliptic.

*Apex.*—Acuminate.

*Base.*—Acute.

*Margin.*—Entire; mostly flat with some broad undulations.

*Texture, upper and lower surfaces.*—Smooth, glabrous.

*Venation pattern.*—Pinnate.

*Color.*—Developing leaves, upper surface: Ground color, between 147B to 137B; venal areas, 191A to 191B; center of leaf, 191C. Venation: Midrib, 191C; primary veins, 191A to 191C. Developing leaves, lower surface: 147B to 147C. Venation: Midrib, 147C to 147D; primary veins, 147B to 147C. Fully expanded leaves, upper surface: Ground color, between 147A to 137A; venal areas, 191A; center of leaf, 191B to 191C. Venation: Midrib, 191B to 191C; primary veins, 191A to 191C. Fully expanded leaves, lower surface: 147B. Venation: Midrib, 147C; primary veins, 147B.

*Petiole.*—Aspect: Mostly erect, outwardly arching to about 25° from vertical with development. Length: About 14.5 cm. Diameter, distal: About 5 mm. Diameter, proximal, flattened: About 3.3 cm. Strength: Strong; flexible. Color, distal: 147C. Color, proximal: 147C to 147D; area adjacent to stem, 155C. Wing length: About 9.4 cm. Wing diameter, base: About 1.25 cm. Wing color, inner surface: 147D. Wing color, outer surface: 147C to 147D; area adjacent to stem, 155C.

Inflorescence description: Inflorescences have not been observed on plants of the new *Aglaonema*.

Disease/pest resistance: Plants of the new *Aglaonema* have not been observed to be resistant to pathogens or pests common to *Aglaonema*.

Temperature tolerance:

Plants of the new *Aglaonema* have been observed to be tolerant to temperatures ranging from about 13° C. to about 40° C. for several hours.

It is claimed:

1. A new and distinct *Aglaonema* plant named 'UFSB2' as illustrated and described.

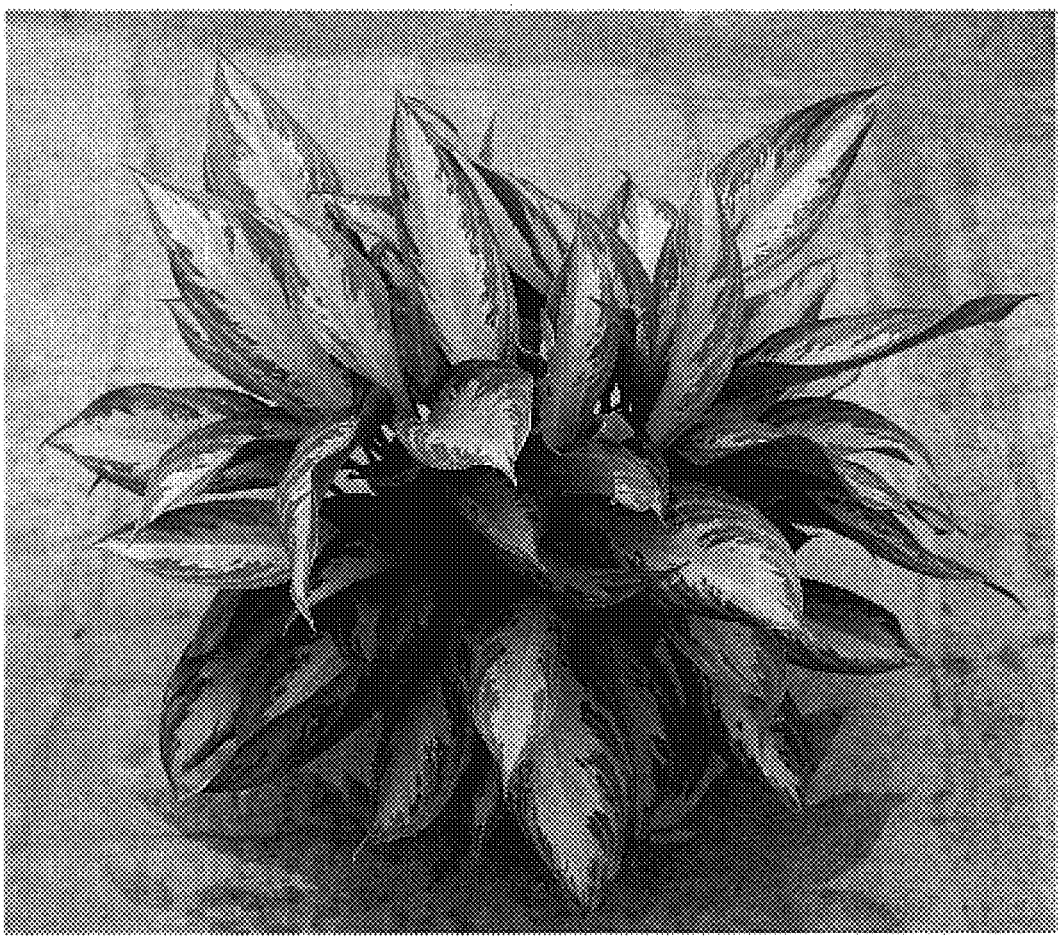

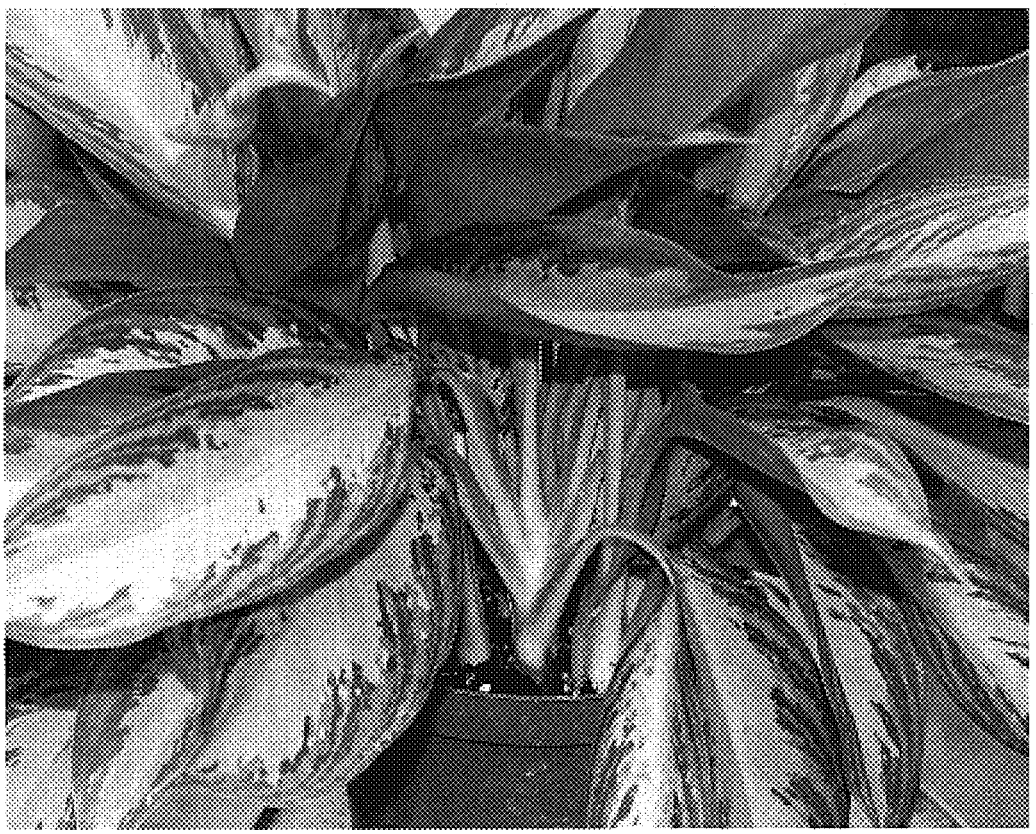

* * * * *